US009022031B2

(12) United States Patent
Nakai et al.

(10) Patent No.: US 9,022,031 B2
(45) Date of Patent: May 5, 2015

(54) USING ESTIMATED CARINAL PRESSURE FOR FEEDBACK CONTROL OF CARINAL PRESSURE DURING VENTILATION

(75) Inventors: Richard Nakai, Long Beach, CA (US); Periagounder Arul, Irvine, CA (US); David Hyde, Oceanside, CA (US)

(73) Assignee: Covidien LP, Boulder, CO (US)

(*) Notice: Subject to any disclaimer, the term of this patent is extended or adjusted under 35 U.S.C. 154(b) by 563 days.

(21) Appl. No.: 13/362,085

(22) Filed: Jan. 31, 2012

(65) Prior Publication Data
US 2013/0192599 A1    Aug. 1, 2013

(51) Int. Cl.
*A61M 16/00* (2006.01)
*A61M 16/10* (2006.01)
*A61M 16/16* (2006.01)

(52) U.S. Cl.
CPC ... *A61M 16/0051* (2013.01); *A61M 2016/0027* (2013.01); *A61M 2016/0036* (2013.01);
(Continued)

(58) Field of Classification Search
CPC ............ A61M 16/00; A61M 16/0051; A61M 16/0875; A61M 16/0057; A61M 16/04; A61M 16/0666; A61M 16/0816; A61M 16/205; A61M 16/0063; A61M 16/12; A61M 16/20; A61M 16/204; G06F 3/0484; G06F 19/3406; G06F 19/3481; G06F 19/345; H01M 10/488; H01M 10/482; G09G 3/3426; G09G 3/3648; A61B 5/0803; A61B 5/087; A61B 5/746; A61B 5/7435; A61B 5/743; A61B 5/4836; A61B 5/0871; A61B 5/085; A61B 5/02416; A61B 5/0816
USPC ............ 128/200.24, 204.18, 204.21, 204.23, 128/202.16, 203.12, 202.22, 204.22, 128/205.24, 205.25, 204.29, 204.24, 128/205.23, 903, 898; 600/300, 301, 323, 600/324, 365, 529, 538; 715/77, 780, 716, 715/781; 702/51, 22; 340/500, 611, 614, 340/626, 679, 286.07, 539.12, 573.1; 324/426; 320/118, 124, 125, 132, 134, 320/426; 434/308; 345/1.2
See application file for complete search history.

(56) References Cited

U.S. PATENT DOCUMENTS 3,827,433 A    8/1974 Shannon
3,869,771 A    3/1975 Bollinger
(Continued)

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Annette Dixon
(74) *Attorney, Agent, or Firm* — Merchant & Gould P.C.

(57) ABSTRACT

This disclosure describes systems and methods for configuring a ventilator to estimate the carinal pressure to minimize the work of breathing due to a breathing tube. A patient's carina is a cartilaginous ridge located at the site of the tracheal bifurcation between the two primary bronchi. An estimated carinal pressure (a pressure estimated to exist at the patient carina) may be determined and used as feedback control for the carinal pressure. According to embodiments, the estimated carinal pressure may be compared to the carinal pressure command to determine an error. The carinal pressure command may be positive end expiratory pressure (PEEP) or some other suitable target pressure. The error between the estimated carinal pressure and the carinal pressure command may then be used as feedback control to achieve the carinal pressure command and thereby to minimize the work of breathing due to the breathing tube.

20 Claims, 5 Drawing Sheets

(52) U.S. Cl.
CPC .... *A61M2016/102* (2013.01); *A61M 2205/505* (2013.01); *A61M 2230/43* (2013.01); *A61M 16/161* (2014.02)

(56) References Cited

U.S. PATENT DOCUMENTS

| | | |
|---|---|---|
| 3,889,670 A | 6/1975 | Loveland et al. |
| 3,896,800 A | 7/1975 | Cibulka |
| 3,908,987 A | 9/1975 | Boehringer |
| 3,976,065 A | 8/1976 | Durkan |
| 4,020,834 A | 5/1977 | Bird |
| 4,050,458 A | 9/1977 | Friend |
| 4,057,059 A | 11/1977 | Reid, Jr. et al. |
| 4,082,093 A | 4/1978 | Fry et al. |
| 4,155,357 A | 5/1979 | Dahl |
| 4,197,843 A | 4/1980 | Bird |
| 4,206,754 A | 6/1980 | Cox et al. |
| 4,211,221 A | 7/1980 | Schwanbom et al. |
| 4,211,239 A | 7/1980 | Raemer et al. |
| 4,227,523 A | 10/1980 | Warnow et al. |
| 4,232,666 A | 11/1980 | Savelli et al. |
| 4,245,633 A | 1/1981 | Erceg |
| 4,265,237 A | 5/1981 | Schwanbom et al. |
| 4,267,827 A | 5/1981 | Racher et al. |
| 4,285,340 A | 8/1981 | Gezari et al. |
| 4,320,754 A | 3/1982 | Watson et al. |
| 4,323,064 A | 4/1982 | Hoenig et al. |
| 4,351,328 A | 9/1982 | Bodai |
| 4,351,329 A | 9/1982 | Ellestad et al. |
| 4,417,573 A | 11/1983 | De Vries |
| 4,436,090 A | 3/1984 | Darling |
| 4,457,304 A | 7/1984 | Molnar et al. |
| 4,459,982 A | 7/1984 | Fry |
| 4,459,983 A | 7/1984 | Beyreuther et al. |
| 4,462,397 A | 7/1984 | Suzuki |
| 4,502,481 A | 3/1985 | Christian |
| 4,527,557 A | 7/1985 | DeVries et al. |
| 4,596,246 A | 6/1986 | Lyall |
| 4,598,706 A | 7/1986 | Darowski et al. |
| 4,611,591 A | 9/1986 | Inui et al. |
| 4,622,976 A | 11/1986 | Timpe et al. |
| 4,651,731 A | 3/1987 | Vicenzi et al. |
| 4,752,089 A | 6/1988 | Carter |
| 4,813,409 A | 3/1989 | Ismach |
| 4,821,709 A | 4/1989 | Jensen |
| 4,877,023 A | 10/1989 | Zalkin |
| 4,921,642 A | 5/1990 | LaTorraca |
| 4,924,862 A | 5/1990 | Levinson |
| 4,954,799 A | 9/1990 | Kumar |
| 5,002,050 A | 3/1991 | McGinnis |
| 5,007,420 A | 4/1991 | Bird |
| 5,057,822 A | 10/1991 | Hoffman |
| 5,063,925 A | 11/1991 | Frank et al. |
| 5,065,746 A | 11/1991 | Steen |
| 5,067,487 A | 11/1991 | Bauman |
| 5,072,737 A | 12/1991 | Goulding |
| 5,150,291 A | 9/1992 | Cummings et al. |
| 5,158,569 A | 10/1992 | Strickland et al. |
| 5,161,525 A | 11/1992 | Kimm et al. |
| 5,222,491 A | 6/1993 | Thomas |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,667 A | 4/1994 | McGrail et al. |
| 5,301,921 A | 4/1994 | Kumar |
| 5,303,698 A | 4/1994 | Tobia et al. |
| 5,315,989 A | 5/1994 | Tobia |
| 5,319,540 A | 6/1994 | Isaza et al. |
| 5,323,772 A | 6/1994 | Linden et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,373,842 A | 12/1994 | Olsson et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,433,193 A | 7/1995 | Sanders et al. |
| 5,438,980 A | 8/1995 | Phillips |
| 5,443,075 A | 8/1995 | Holscher |
| 5,487,383 A | 1/1996 | Levinson |
| 5,507,282 A | 4/1996 | Younes |
| 5,509,406 A | 4/1996 | Kock et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brody |
| 5,544,674 A | 8/1996 | Kelly |
| 5,549,106 A | 8/1996 | Gruenke et al. |
| 5,551,419 A | 9/1996 | Froehlich et al. |
| 5,575,283 A | 11/1996 | Sjoestrand |
| 5,582,163 A | 12/1996 | Bonassa |
| 5,596,984 A | 1/1997 | O'Mahoney et al. |
| 5,606,968 A | 3/1997 | Mang |
| 5,615,669 A | 4/1997 | Olsson et al. |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,647,345 A | 7/1997 | Saul |
| 5,647,351 A | 7/1997 | Weismann et al. |
| 5,651,360 A | 7/1997 | Tobia |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,715,812 A | 2/1998 | Deighan et al. |
| 5,735,267 A | 4/1998 | Tobia |
| 5,740,796 A | 4/1998 | Skog |
| 5,752,509 A | 5/1998 | Lachmann et al. |
| 5,762,480 A | 6/1998 | Adahan |
| 5,769,072 A | 6/1998 | Olsson et al. |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,865,173 A | 2/1999 | Froehlich |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,934,274 A | 8/1999 | Merrick et al. |
| 5,970,975 A | 10/1999 | Estes et al. |
| 5,983,891 A | 11/1999 | Fukunaga |
| 6,010,459 A | 1/2000 | Silkoff et al. |
| 6,024,089 A | 2/2000 | Wallace et al. |
| 6,029,664 A | 2/2000 | Zdrojkowski et al. |
| 6,041,780 A | 3/2000 | Richard et al. |

(56) References Cited

U.S. PATENT DOCUMENTS

| | | | |
|---|---|---|---|
| 6,042,550 | A | 3/2000 | Haryadi et al. |
| 6,047,860 | A | 4/2000 | Sanders |
| 6,067,984 | A | 5/2000 | Piper |
| 6,076,523 | A | 6/2000 | Jones et al. |
| 6,095,139 | A | 8/2000 | Psaros |
| 6,095,140 | A | 8/2000 | Poon et al. |
| 6,102,038 | A | 8/2000 | DeVries |
| 6,105,575 | A | 8/2000 | Estes et al. |
| 6,116,240 | A | 9/2000 | Merrick et al. |
| 6,116,464 | A | 9/2000 | Sanders |
| 6,123,073 | A | 9/2000 | Schlawin et al. |
| 6,135,106 | A | 10/2000 | Dirks et al. |
| 6,142,150 | A | 11/2000 | O'Mahony |
| 6,148,814 | A | 11/2000 | Clemmer et al. |
| 6,152,132 | A | 11/2000 | Psaros |
| 6,158,432 | A | 12/2000 | Biondi et al. |
| 6,161,539 | A | 12/2000 | Winter |
| 6,192,885 | B1 | 2/2001 | Jalde |
| 6,200,271 | B1 | 3/2001 | Kuck et al. |
| 6,210,342 | B1 | 4/2001 | Kuck et al. |
| 6,213,119 | B1 | 4/2001 | Brydon et al. |
| 6,217,524 | B1 | 4/2001 | Orr et al. |
| 6,220,244 | B1 | 4/2001 | McLaughlin |
| 6,220,245 | B1 | 4/2001 | Takabayashi et al. |
| 6,238,351 | B1 | 5/2001 | Orr et al. |
| 6,241,681 | B1 | 6/2001 | Haryadi et al. |
| 6,258,038 | B1 | 7/2001 | Haryadi et al. |
| 6,269,812 | B1 | 8/2001 | Wallace et al. |
| 6,273,444 | B1 | 8/2001 | Power |
| 6,283,119 | B1 | 9/2001 | Bourdon |
| 6,305,373 | B1 | 10/2001 | Wallace et al. |
| 6,305,374 | B1 | 10/2001 | Zdrojkowski et al. |
| 6,306,098 | B1 | 10/2001 | Orr et al. |
| 6,321,748 | B1 | 11/2001 | O'Mahoney |
| 6,325,785 | B1 | 12/2001 | Babkes et al. |
| 6,357,438 | B1 | 3/2002 | Hansen |
| 6,360,745 | B1 | 3/2002 | Wallace et al. |
| 6,369,838 | B1 | 4/2002 | Wallace et al. |
| 6,390,091 | B1 * | 5/2002 | Banner et al. ............ 128/204.21 |
| 6,412,483 | B1 | 7/2002 | Jones et al. |
| 6,427,692 | B1 | 8/2002 | Hoglund |
| 6,439,229 | B1 | 8/2002 | Du et al. |
| 6,443,154 | B1 | 9/2002 | Jalde et al. |
| 6,450,968 | B1 | 9/2002 | Wallen et al. |
| 6,467,477 | B1 | 10/2002 | Frank et al. |
| 6,467,478 | B1 | 10/2002 | Merrick et al. |
| 6,510,846 | B1 | 1/2003 | O'Rourke |
| 6,532,957 | B2 | 3/2003 | Berthon-Jones |
| 6,532,960 | B1 | 3/2003 | Yurko |
| 6,539,940 | B2 | 4/2003 | Zdrojkowski et al. |
| 6,546,930 | B1 | 4/2003 | Emerson et al. |
| 6,553,991 | B1 | 4/2003 | Isaza |
| 6,557,553 | B1 | 5/2003 | Borrello |
| 6,564,798 | B1 | 5/2003 | Jalde |
| 6,568,387 | B2 | 5/2003 | Davenport et al. |
| 6,571,795 | B2 | 6/2003 | Bourdon |
| 6,584,973 | B1 | 7/2003 | Biondi et al. |
| 6,588,422 | B1 | 7/2003 | Berthon-Jones et al. |
| 6,609,517 | B1 | 8/2003 | Estes et al. |
| 6,622,726 | B1 | 9/2003 | Du |
| 6,626,175 | B2 | 9/2003 | Jafari et al. |
| 6,640,806 | B2 | 11/2003 | Yurko |
| 6,644,310 | B1 | 11/2003 | Delache et al. |
| 6,659,100 | B2 | 12/2003 | O'Rourke |
| 6,662,032 | B1 | 12/2003 | Gavish et al. |
| 6,668,824 | B1 | 12/2003 | Isaza et al. |
| 6,675,801 | B2 | 1/2004 | Wallace et al. |
| 6,679,258 | B1 | 1/2004 | Strom |
| 6,688,307 | B2 | 2/2004 | Berthon-Jones |
| 6,705,314 | B1 | 3/2004 | O'Dea |
| 6,718,974 | B1 | 4/2004 | Moberg |
| 6,725,447 | B1 | 4/2004 | Gilman et al. |
| 6,739,337 | B2 | 5/2004 | Isaza |
| 6,752,151 | B2 | 6/2004 | Hill |
| 6,758,216 | B1 | 7/2004 | Berthon-Jones et al. |
| 6,761,167 | B1 | 7/2004 | Nadjafizadeh et al. |
| 6,761,168 | B1 | 7/2004 | Nadjafizadeh et al. |
| 6,776,159 | B2 | 8/2004 | Pelerossi et al. |
| 6,786,216 | B2 | 9/2004 | O'Rourke |
| 6,810,876 | B2 | 11/2004 | Berthon-Jones |
| 6,814,074 | B1 | 11/2004 | Nadjafizadeh et al. |
| 6,823,866 | B2 | 11/2004 | Jafari et al. |
| 6,854,462 | B2 | 2/2005 | Berthon-Jones et al. |
| 6,866,040 | B1 | 3/2005 | Bourdon |
| 6,915,803 | B2 | 7/2005 | Berthon-Jones et al. |
| 6,920,878 | B2 | 7/2005 | Sinderby et al. |
| 6,932,084 | B2 | 8/2005 | Estes et al. |
| 6,948,497 | B2 | 9/2005 | Zdrojkowski et al. |
| 6,960,854 | B2 | 11/2005 | Nadjafizadeh et al. |
| 6,962,155 | B1 | 11/2005 | Sinderby |
| 6,986,349 | B2 | 1/2006 | Lurie |
| 6,990,980 | B2 | 1/2006 | Richey, II |
| 7,000,612 | B2 | 2/2006 | Jafari et al. |
| 7,036,504 | B2 | 5/2006 | Wallace et al. |
| 7,066,177 | B2 | 6/2006 | Pittaway et al. |
| 7,077,131 | B2 | 7/2006 | Hansen |
| RE39,225 | E | 8/2006 | Isaza et al. |
| 7,096,866 | B2 | 8/2006 | Be'eri et al. |
| 7,117,438 | B2 | 10/2006 | Wallace et al. |
| 7,121,277 | B2 | 10/2006 | Ström |
| 7,122,010 | B2 | 10/2006 | Böhm et al. |
| 7,128,069 | B2 | 10/2006 | Farrugia et al. |
| 7,137,389 | B2 | 11/2006 | Berthon-Jones |
| 7,152,598 | B2 | 12/2006 | Morris et al. |
| 7,204,251 | B2 | 4/2007 | Lurie |
| 7,246,618 | B2 | 7/2007 | Habashi |
| 7,267,122 | B2 | 9/2007 | Hill |
| 7,267,652 | B2 | 9/2007 | Coyle et al. |
| 7,270,126 | B2 | 9/2007 | Wallace et al. |
| 7,270,128 | B2 | 9/2007 | Berthon-Jones et al. |
| 7,296,573 | B2 | 11/2007 | Estes et al. |
| 7,369,757 | B2 | 5/2008 | Farbarik |
| 7,370,650 | B2 | 5/2008 | Nadjafizadeh et al. |
| 7,428,902 | B2 | 9/2008 | Du et al. |
| 7,460,959 | B2 | 12/2008 | Jafari |
| 7,465,275 | B2 | 12/2008 | Stenqvist |
| 7,472,702 | B2 | 1/2009 | Beck et al. |
| 7,478,634 | B2 | 1/2009 | Jam |
| 7,481,222 | B2 | 1/2009 | Reissmann |
| 7,487,773 | B2 | 2/2009 | Li |
| RE40,814 | E | 6/2009 | Van Brunt et al. |
| 7,556,041 | B2 | 7/2009 | Madsen |
| 7,562,657 | B2 | 7/2009 | Blanch et al. |
| 7,588,033 | B2 | 9/2009 | Wondka |
| 7,617,824 | B2 | 11/2009 | Doyle |
| 7,621,270 | B2 | 11/2009 | Morris et al. |
| 7,644,713 | B2 | 1/2010 | Berthon-Jones |
| 7,654,802 | B2 | 2/2010 | Crawford, Jr. et al. |
| 7,686,019 | B2 | 3/2010 | Weiss et al. |
| 7,694,677 | B2 | 4/2010 | Tang |
| 7,708,015 | B2 | 5/2010 | Seeger et al. |
| 7,717,113 | B2 | 5/2010 | Andrieux |
| 7,717,858 | B2 | 5/2010 | Massad |
| D618,356 | S | 6/2010 | Ross |
| 7,735,492 | B2 | 6/2010 | Doshi et al. |
| 7,784,461 | B2 | 8/2010 | Figueiredo et al. |
| 7,793,656 | B2 | 9/2010 | Johnson |
| 7,798,148 | B2 | 9/2010 | Doshi et al. |
| 7,802,571 | B2 | 9/2010 | Tehrani |
| 7,806,120 | B2 | 10/2010 | Loomas et al. |
| 7,810,496 | B2 | 10/2010 | Estes et al. |
| 7,810,497 | B2 | 10/2010 | Pittman et al. |
| 7,823,588 | B2 | 11/2010 | Hansen |
| 7,841,347 | B2 | 11/2010 | Sonnenschein et al. |
| 7,855,716 | B2 | 12/2010 | McCreary et al. |
| D632,796 | S | 2/2011 | Ross et al. |
| D632,797 | S | 2/2011 | Ross et al. |
| 7,886,739 | B2 | 2/2011 | Soliman et al. |
| 7,891,354 | B2 | 2/2011 | Farbarik |
| 7,893,560 | B2 | 2/2011 | Carter |
| 7,909,034 | B2 | 3/2011 | Sinderby et al. |
| D638,852 | S | 5/2011 | Skidmore et al. |
| 7,938,114 | B2 | 5/2011 | Matthews et al. |
| 7,971,589 | B2 | 7/2011 | Mashak et al. |

(56) References Cited

U.S. PATENT DOCUMENTS

| | | | |
|---|---|---|---|
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 8,001,967 B2 | 8/2011 | Wallace et al. |
| D645,158 S | 9/2011 | Sanchez et al. |
| 8,011,363 B2 | 9/2011 | Johnson |
| 8,011,364 B2 | 9/2011 | Johnson |
| 8,011,366 B2 | 9/2011 | Knepper |
| 8,015,974 B2 | 9/2011 | Christopher et al. |
| 8,020,558 B2 | 9/2011 | Christopher et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| 8,792,949 B2 | 7/2014 | Baker, Jr. |
| 2002/0017301 A1 | 2/2002 | Lundin |
| 2002/0026941 A1 | 3/2002 | Biondi et al. |
| 2002/0117173 A1 | 8/2002 | Lynn et al. |
| 2002/0144681 A1 | 10/2002 | Cewers et al. |
| 2003/0029453 A1 | 2/2003 | Smith et al. |
| 2003/0140925 A1 | 7/2003 | Sapienza et al. |
| 2003/0225339 A1 | 12/2003 | Orr et al. |
| 2005/0034724 A1 | 2/2005 | O'Dea |
| 2005/0039748 A1 | 2/2005 | Andrieux |
| 2005/0139212 A1 | 6/2005 | Bourdon |
| 2005/0166928 A1 | 8/2005 | Jiang |
| 2006/0249153 A1 | 11/2006 | DeVries et al. |
| 2006/0272637 A1 | 12/2006 | Johnson |
| 2006/0283451 A1 | 12/2006 | Albertelli |
| 2007/0017515 A1 | 1/2007 | Wallace et al. |
| 2007/0017518 A1 | 1/2007 | Farrugia et al. |
| 2007/0017522 A1 | 1/2007 | Be-Eri et al. |
| 2007/0017523 A1 | 1/2007 | Be-Eri et al. |
| 2007/0062532 A1 | 3/2007 | Choncholas |
| 2007/0062533 A1 | 3/2007 | Choncholas et al. |
| 2007/0068528 A1 | 3/2007 | Bohm et al. |
| 2007/0077200 A1 | 4/2007 | Baker |
| 2007/0089741 A1 | 4/2007 | Bohm et al. |
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0000475 A1 | 1/2008 | Hill |
| 2008/0041383 A1 | 2/2008 | Matthews et al. |
| 2008/0045845 A1 | 2/2008 | Pfeiffer et al. |
| 2008/0053441 A1 | 3/2008 | Gottlib et al. |
| 2008/0060656 A1 | 3/2008 | Isaza |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0072904 A1 | 3/2008 | Becker et al. |
| 2008/0078390 A1 | 4/2008 | Milne et al. |
| 2008/0078395 A1 | 4/2008 | Ho et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0168990 A1 | 7/2008 | Cooke et al. |
| 2008/0178874 A1 | 7/2008 | Doshi et al. |
| 2008/0196720 A1 | 8/2008 | Kollmeyer et al. |
| 2008/0200775 A1 | 8/2008 | Lynn |
| 2008/0202528 A1 | 8/2008 | Carter et al. |
| 2008/0221470 A1 | 9/2008 | Sather et al. |
| 2008/0223361 A1 | 9/2008 | Nieuwstad |
| 2008/0230061 A1 | 9/2008 | Tham |
| 2008/0230062 A1 | 9/2008 | Tham |
| 2008/0236582 A1 | 10/2008 | Tehrani |
| 2008/0314385 A1 | 12/2008 | Brunner et al. |
| 2009/0007914 A1 | 1/2009 | Bateman |
| 2009/0020119 A1 | 1/2009 | Eger et al. |
| 2009/0114223 A1 | 5/2009 | Bonassa |
| 2009/0137919 A1 | 5/2009 | Bar-Lavie et al. |
| 2009/0145441 A1 | 6/2009 | Doshi et al. |
| 2009/0159082 A1 | 6/2009 | Eger |
| 2009/0165795 A1 | 7/2009 | Nadjafizadeh et al. |
| 2009/0165798 A1 | 7/2009 | Cong et al. |
| 2009/0171176 A1 | 7/2009 | Andersohn |
| 2009/0194109 A1 | 8/2009 | Doshi et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. et al. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0266360 A1 | 10/2009 | Acker et al. |
| 2009/0272381 A1 | 11/2009 | Dellaca et al. |
| 2009/0277448 A1 | 11/2009 | Ahlmén et al. |
| 2009/0293872 A1 | 12/2009 | Bocke |
| 2009/0293877 A1 | 12/2009 | Blanch et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0301492 A1 | 12/2009 | Wysocki et al. |
| 2009/0308398 A1 | 12/2009 | Ferdinand et al. |
| 2009/0314297 A1 | 12/2009 | Mathews |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078018 A1 | 4/2010 | Heinonen et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0101575 A1 | 4/2010 | Fedorko et al. |
| 2010/0108066 A1 | 5/2010 | Martin et al. |
| 2010/0116270 A1 | 5/2010 | Edwards et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0241159 A1 | 9/2010 | Li |
| 2010/0242961 A1 | 9/2010 | Mougel et al. |
| 2010/0249549 A1 | 9/2010 | Baker, Jr. et al. |
| 2010/0252046 A1 | 10/2010 | Dahlström et al. |
| 2010/0275920 A1 | 11/2010 | Tham et al. |
| 2010/0275921 A1 | 11/2010 | Schindhelm et al. |
| 2010/0282259 A1 | 11/2010 | Figueiredo et al. |
| 2010/0288283 A1 | 11/2010 | Campbell et al. |
| 2010/0300445 A1 | 12/2010 | Chatburn et al. |
| 2010/0300446 A1 | 12/2010 | Nicolazzi et al. |
| 2010/0319691 A1 | 12/2010 | Lurie et al. |

(56) References Cited

U.S. PATENT DOCUMENTS

| | | |
|---|---|---|
| 2010/0326447 A1 | 12/2010 | Loomas et al. |
| 2010/0331877 A1 | 12/2010 | Li et al. |
| 2011/0005530 A1 | 1/2011 | Doshi et al. |
| 2011/0009762 A1 | 1/2011 | Eichler et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1* | 2/2011 | Thiessen ............... 715/771 |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0061650 A1 | 3/2011 | Heesch |
| 2011/0073112 A1 | 3/2011 | DiBlasi et al. |
| 2011/0088697 A1 | 4/2011 | DeVries et al. |
| 2011/0100365 A1 | 5/2011 | Wedler et al. |
| 2011/0108041 A1 | 5/2011 | Sather et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197884 A1 | 8/2011 | Duff et al. |
| 2011/0197886 A1 | 8/2011 | Guttmann et al. |
| 2011/0197892 A1 | 8/2011 | Koledin |
| 2011/0203598 A1 | 8/2011 | Favet et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0226248 A1 | 9/2011 | Duff et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

\* cited by examiner

USING ESTIMATED CARINAL PRESSURE FOR FEEDBACK CONTROL OF CARINAL PRESSURE DURING VENTILATION

INTRODUCTION

A ventilator is a device that mechanically helps patients breathe by replacing some or all of the muscular effort required to inflate and deflate the lungs. When delivering positive-pressure ventilation, the ventilator may be configured with a number of target pressures, including an inspiratory pressure (i.e., the target pressure to be delivered to the patient during inspiration) and an end-expiratory pressure (i.e., the target pressure at the end of exhalation). In some cases, a clinician may desire the baseline pressure to be positive, termed positive end-expiratory pressure (PEEP). Among other things, PEEP may promote higher oxygenation saturation and/or may prevent alveolar collapse during expiration. It is desirable that the carinal pressure be maintained at PEEP during inspiration so that the patient has the sense of breathing without the restriction imposed by the breathing tube.

Clinicians and patients may greatly benefit from a determination of an estimated carinal pressure as feedback control for maintaining the carinal pressure at PEEP in order to minimize the work of breathing due to the breathing tube. Additionally, a determination of an estimated carinal pressure may be used as feedback control for maintaining the carinal pressure at any other suitable target pressure.

Using Estimated Carinal Pressure for Feedback Control of Carinal Pressure During Ventilation This disclosure describes systems and methods for configuring a ventilator to estimate the carinal pressure to minimize the work of breathing due to a breathing tube. A patient's carina is a cartilaginous ridge located at the site of the tracheal bifurcation between the two primary bronchi. According to embodiments, an estimated carinal pressure may be determined and used as feedback control for the carinal pressure. An estimated carinal pressure refers to a pressure estimated to exist at the patient carina. According to embodiments, the estimated carinal pressure may be compared to the carinal pressure command to determine an error. The carinal pressure command may be positive end expiratory pressure (PEEP), a function of PEEP, or some other suitable target pressure. The PEEP or other suitable target pressure may be set by a clinician for a particular patient based on a medical protocol, a medical prescription, or otherwise. The error between the estimated carinal pressure and the carinal pressure command may then be used as feedback control to achieve the carinal pressure command and thereby to minimize the work of breathing due to the breathing tube.

According to embodiments, a ventilator-implemented method for controlling delivery of gas flow to a patient is provided. The method comprises delivering gas flow to the patient based on a carinal pressure command. The method further comprises receiving a signal representative of a pressure at a patient wye and calculating a pressure drop across a breathing tube extending from the patient wye to about the carina of the patient. Additionally, the method comprises estimating a carinal pressure by subtracting the pressure drop across the breathing tube from the pressure at the patient wye and comparing the estimated carinal pressure to the carinal pressure command. The method further comprises controlling delivery of gas flow to the patient based on comparing the estimated carinal pressure and the carinal pressure command.

According to additional embodiments, a ventilator system for controlling delivery of gas flow to a patient is provided. The ventilator system comprises at least one processor and at least one memory communicatively coupled to the at least one processor and containing instructions that, when executed by the at least one processor, cause the ventilator system to perform a method. The method comprises delivering gas flow to the patient based on a carinal pressure command. The method further comprises receiving a signal representative of a pressure at a patient wye and calculating a pressure drop across a breathing tube extending from the patient wye to about the carina of the patient. In addition, the method comprises estimating a carinal pressure by subtracting the pressure drop across the breathing tube from the pressure at the patient wye and comparing the estimated carinal pressure to the carinal pressure command. The method further comprises controlling delivery of gas flow to the patient based on comparing the estimated carinal pressure and the carinal pressure command.

According to additional embodiments, a ventilator processing interface for controlling delivery of gas flow to a patient is provided. The ventilator processing interface comprising means for delivering gas flow to the patient based on a carinal pressure command. The ventilator processing interface further comprising means for receiving a signal representative of a pressure at a patient wye and means for calculating a pressure drop across a breathing tube extending from the patient wye to about the carina of the patient. The ventilator processing interface also comprising means for estimating a carinal pressure by subtracting the pressure drop across the breathing tube from the pressure at the patient wye and means for comparing the estimated carinal pressure to the carinal pressure command. Additionally, the ventilator processing interface comprising means for controlling delivery of gas flow to the patient based on comparing the estimated carinal pressure and the carinal pressure command.

According to additional embodiments, a non-transitory computer storage medium having computer-executable instructions for performing steps is provided. The steps comprising delivering gas flow to the patient based on a carinal pressure command. The steps further comprising receiving a signal representative of a pressure at a patient wye and calculating a pressure drop across a breathing tube extending from the patient wye to about the carina of the patient. The steps also comprising estimating a carinal pressure by subtracting the pressure drop across the breathing tube from the pressure at the patient wye and comparing the estimated carinal pressure to the carinal pressure command. Additionally, the steps comprising controlling delivery of gas flow to the patient based on comparing the estimated carinal pressure and the carinal pressure command.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the claims.

BRIEF DESCRIPTION OF THE DRAWINGS

The following drawing figures, which form a part of this application, are illustrative of described technology and are

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment for using an estimated pressure as feedback control for a pressure command.

This disclosure describes systems and methods for configuring a ventilator to estimate the carinal pressure to minimize the work of breathing due to a breathing tube. A patient's carina is a cartilaginous ridge located at the site of the tracheal bifurcation between the two primary bronchi. According to embodiments, an estimated carinal pressure may be determined and used as feedback control for maintaining a carinal pressure command. The carinal pressure command may be positive end expiratory pressure (PEEP), a function of PEEP, or some other suitable target pressure. An estimated carinal pressure refers to a pressure estimated to exist at the patient carina. According to embodiments, the estimated carinal pressure may be compared to the carinal pressure command to determine an error. The error between the estimated carinal pressure and the carinal pressure command may then be used as feedback control to achieve the carinal pressure command and thereby to minimize the work of breathing due to the breathing tube.

Figure 1:
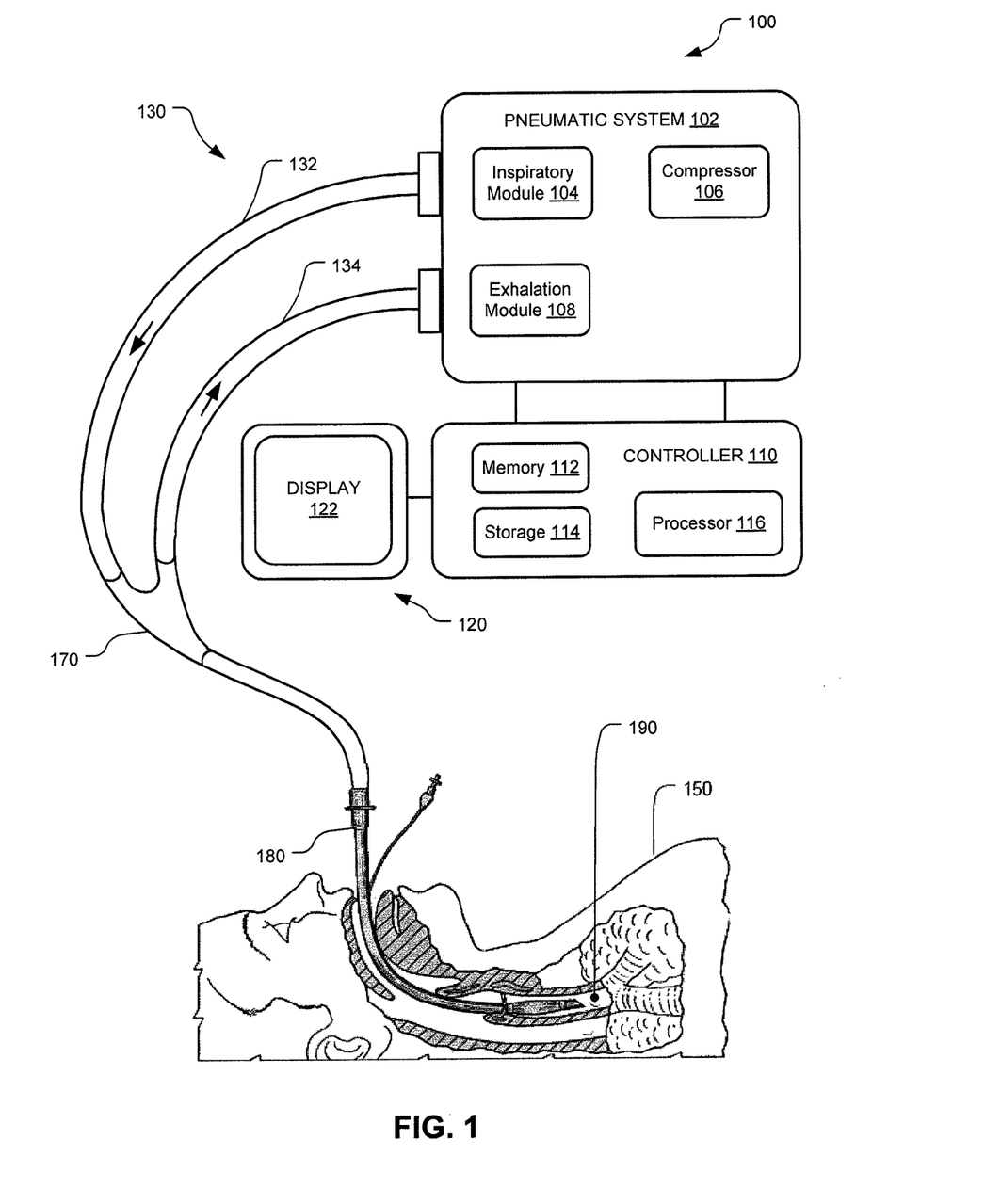
FIG. 1 is a diagram illustrating an embodiment of a ventilator connected to a human patient.

FIG. 1 is a diagram illustrating an embodiment of an exemplary ventilator 100 connected to a human patient 150.

Ventilator 100 includes a pneumatic system 102 (also referred to as a pressure generating system 102) for circulating breathing gases to and from patient 150 via the ventilation tubing system 130, which couples the patient to the pneumatic system via an invasive (e.g., endotracheal tube, as shown, or a tracheostomy tube) or a non-invasive (e.g., nasal mask) patient interface. According to embodiments, a non-invasive patient interface may be less applicable to the present methods and systems, which take into account a pressure drop across an invasive patient interface (i.e., breathing tube).

Ventilation tubing system 130 may be a two-limb (shown) or a one-limb circuit for carrying gases to and from the patient 150. In a two-limb embodiment, a fitting, typically referred to as a "wye-fitting" or "patient wye" 170, may be provided to couple an invasive patient interface 180 (as shown, an endotracheal tube) or a non-invasive (NIV) patient interface (e.g., mask, not shown) to an inspiratory limb 132 and an expiratory limb 134 of the ventilation tubing system 130. According to at least some embodiments, an invasive patient interface may be interchangeably referred to as a "breathing tube" and may include an endotracheal tube, tracheostomy tube, or other invasive patient interface. According to embodiments, the breathing tube extends from the patient wye to about the carina of the patient. The carina 190 of patient 150 is located at the tracheal bifurcation between the two primary bronchi leading into the patient's lungs.

Pneumatic system 102 may be configured in a variety of ways. In the present example, system 102 includes an exhalation module 108 coupled with the expiratory limb 134 and an inhalation module 104 coupled with the inspiratory limb 132. Compressor 106 or other source(s) of pressurized gases (e.g., air, oxygen, and/or helium) is coupled to inhalation module 104 to provide a gas source for ventilatory support via inspiratory limb 132.

The pneumatic system 102 may include a variety of other components, including mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilatory settings, select operational modes, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display 122 to serve both as an input and output device.

The memory 112 includes non-transitory, computer-readable storage media for storing software that is executed by the one or more processors 116 and which controls the operation of the ventilator 100. In an embodiment, the memory 112 includes one or more solid-state storage devices such as flash memory chips. In an alternative embodiment, the memory 112 may be mass storage connected to the one or more processors 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the one or more processors 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory system or between the ventilatory system and other therapeutic equipment and/or remote monitoring systems may be conducted over a distributed network via wired or wireless means. Further, the present methods may be configured as a presentation layer built over the TCP/IP protocol. TCP/IP stands for "Transmission Control Protocol/Internet Protocol" and provides a basic communication language for many local networks (such as intra- or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Figure 2:
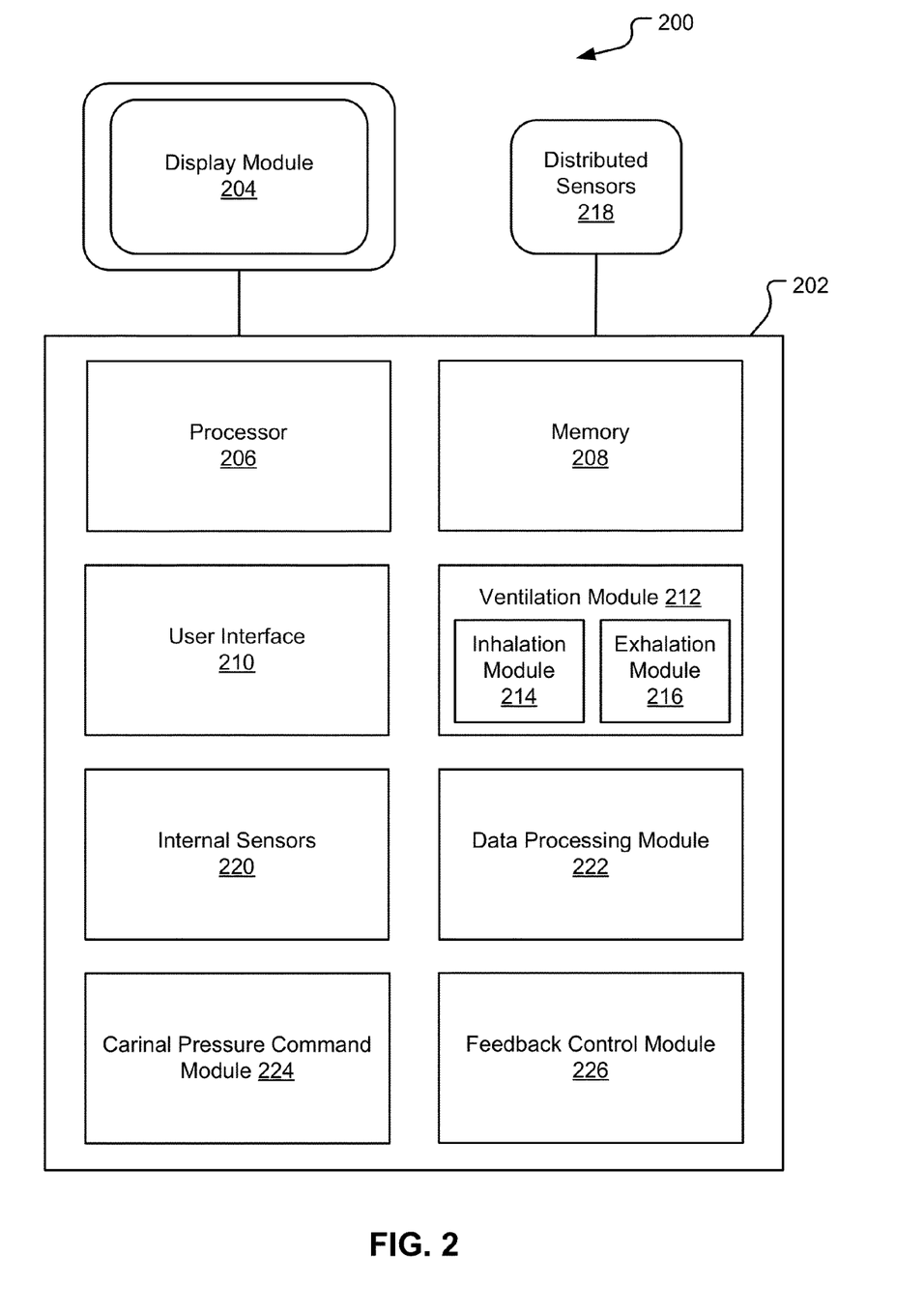
FIG. 2 is a block-diagram illustrating an embodiment of a ventilatory system for estimating carinal pressure and using the estimated carinal pressure as feedback control.

FIG. 2 is a block-diagram illustrating an embodiment of a ventilatory system for estimating carinal pressure and using the estimated carinal pressure as feedback control.

Ventilatory system 200 includes ventilator 202 with its various modules and components. That is, ventilator 202 may further include, inter alia, one or more processors 206, memory 208, user interface 210, and ventilation module 212 (which may further include and/or communicate with inspiration module 214 and exhalation module 216). The one or more processors 206 are defined as described above for one or more processors 116. Processors 206 may further be configured with a clock whereby elapsed time may be monitored by the system 200. Memory 208 is defined as described above for memory 112.

The ventilatory system 200 may also include a display module 204 communicatively coupled to ventilator 202. Display module 204 may provide various input screens, for receiving clinician input, and various display screens, for presenting useful information to the clinician. The display module 204 is configured to communicate with user interface 210 and may include a graphical user interface (GUI). The GUI may be an interactive display, e.g., a touch-sensitive screen or otherwise, and may provide various windows (i.e., visual areas) comprising elements for receiving user input and interface command operations and for displaying ventilatory information (e.g., ventilatory data, alerts, patient information, parameter settings, etc.). The elements may include controls, graphics, charts, tool bars, input fields, etc. Alternatively, other suitable means of communication with the ventilator 202 may be provided, for instance by a wheel, keyboard, mouse, or other suitable interactive device. Thus, user interface 210 may accept commands and input through display module 204. Display module 204 may also provide useful information in the form of various ventilatory data regarding the physical condition of a patient and/or a prescribed respiratory treatment. The useful information may be derived by the ventilator 202, based on data collected by a data processing module 222, and the useful information may be displayed to the clinician on display module 204 in the form of graphs, wave representations, pie graphs, or other suitable forms of graphic display.

Ventilation module 212 may oversee ventilation of a patient according to ventilatory settings. Ventilatory settings may include any appropriate input for configuring the ventilator to deliver breathable gases to a particular patient. Ventilatory settings may be entered by a clinician, e.g., based on a prescribed treatment protocol for the particular patient, or automatically generated by the ventilator, e.g., based on attributes (i.e., age, diagnosis, ideal body weight, gender, etc.) of the particular patient according to any appropriate standard protocol or otherwise. For example, ventilatory settings may include, inter alia, inspiratory pressure ($P_I$), pressure support ($P_{SUPP}$), rise time percent (rise time %), positive end-expiratory pressure (PEEP), etc.

Ventilation module 212 may further include an inspiration module 214 configured to deliver gases to the patient according to prescribed ventilatory settings. Specifically, inspiration module 214 may correspond to or control the inhalation module 104 or may be otherwise coupled to source(s) of pressurized gases (e.g., air, oxygen, and/or helium), and may deliver gases to the patient. Inspiration module 214 may be configured to provide ventilation according to various ventilatory types and modes, e.g., via volume-targeted, pressure-targeted, or via any other suitable type of ventilation. According to some embodiments, inspiration module 214 may be configured to deliver mandatory ventilation to a patient based on a set inspiratory volume or pressure for a set period of time (referred to as the inspiratory time, $T_I$). Alternatively, inspiration module 214 may be configured to deliver spontaneous ventilation to a patient based on an inspiratory pressure support setting. An inspiratory pressure support setting may be a set percentage of ventilation support, a set value of pressure support, or other suitable partial to full ventilation setting. According to additional embodiments, various ventilator control algorithms may control inspiration module 214 maintain a target pressure at the patient carina during inspiration. According to some embodiments, the target pressure may be determined or calculated to minimize the work of breathing due to the breathing tube. According to embodiments, the target pressure may be a carinal pressure command equal to PEEP, some suitable percentage of PEEP, or some other suitable pressure for minimizing the work of breathing due to the breathing tube.

Ventilation module 212 may further include an exhalation module 216 configured to release gases from the patient's lungs according to prescribed ventilatory settings. Specifically, exhalation module 216 may correspond to or control exhalation module 108 or may otherwise be associated with and/or control an exhalation valve for releasing gases from the patient. By way of general overview, a ventilator may initiate exhalation based on lapse of an inspiratory time setting ($T_I$) or other cycling criteria set by the clinician or derived from ventilatory settings. Alternatively, exhalation may be cycled based on detection of patient effort or otherwise. Upon initiating the exhalation phase, exhalation module 216 may allow the patient to exhale by controlling an exhalation valve.

The ventilatory system 200 may also include one or more distributed sensors 218 communicatively coupled to ventilator 202. Distributed sensors 218 may communicate with various components of ventilator 202, e.g., ventilation module 212, internal sensors 220, data processing module 222, carinal pressure command module 224, feedback control module 226, and any other suitable components and/or modules. Distributed sensors 218 may be placed in any suitable location, e.g., within the ventilatory circuitry or other devices communicatively coupled to the ventilator. For example, sensors may be affixed to the ventilatory tubing or may be imbedded in the tubing itself. According to some embodiments, sensors may be provided at or near the carina for detecting a pressure at the carina (e.g., actual carinal pressure). Additionally or alternatively, sensors may be affixed or imbedded in or near patient wye 170 and/or patient interface 180, as described above. A sensor affixed near the patient wye 170 may be configured to measure an actual wye pressure. Distributed sensors 218 may include pressure transducers for detecting circuit pressure, flowmeters for detecting circuit flow, optical or ultrasound sensors for measuring gas characteristics or other parameters, or any other suitable sensory device.

Ventilator 202 may further include one or more internal sensors 220. Similar to distributed sensors 218, internal sensors 220 may communicate with various components of ventilator 202, e.g., ventilation module 212, data processing module 222, carinal pressure command module 224, feedback control module 226, and any other suitable components and/or modules. Internal sensors 220 may employ any suitable sensory or derivative technique for monitoring one or more parameters associated with the ventilation of a patient. However, as opposed to the distributed sensors 218, the internal sensors 220 may be placed in any suitable internal location, such as, within the ventilatory circuitry or within components or modules of ventilator 202. For example, sensors may be coupled to the inhalation and/or exhalation modules, the exhalation valve, etc., for detecting pressure and/or flow. Specifically, internal sensors may include pressure transducers and flowmeters for measuring changes in pressure and airflow. Additionally or alternatively, internal sensors may utilize optical or ultrasound techniques for measuring changes in ventilatory parameters.

Ventilator 202 may further include a data processing module 222. As noted above, distributed sensors 218 and/or internal sensors 220 may collect data regarding various ventilatory parameters. A ventilatory parameter refers to any factor, characteristic, or measurement associated with the ventilation of a patient, whether monitored by the ventilator or by any other device. According to embodiments, internal and/or distributed sensors may further transmit collected data to the data processing module 222 and the data processing module 222 may be configured to measure data regarding some ventilatory parameters, to retrieve data regarding some ventilatory parameters or settings, to calculate data regarding other ventilatory parameters, and/or to graphically represent measured, retrieved, and/or calculated data on display module 204. According to embodiments, any measured, retrieved, calculated, and/or graphically represented data may be referred to as ventilatory data.

For example, according to some embodiments, the ventilator may periodically or continuously measure ventilatory data associated with pressure and/or flow in the patient circuit or in the breathing tube. According to additional embodiments, the ventilator may retrieve ventilatory data associated with ventilatory settings (e.g., $O_2$%, PEEP, $P_I$, $P_{SUPP}$, etc.), patient data (e.g., ideal body weight, IBW), breathing tube data (e.g., diameter, length, type, and/or resistance of breathing tube), atmospheric pressure data (e.g., measured or default of 0 cm$H_2O$), humidity data (e.g., measured or default of 100% saturation), etc. Retrieved ventilatory data may be acquired from any suitable database or data storage location associated with the ventilator (e.g., stored in memory 208, stored on a server accessible over a network, etc.). According to additional embodiments, the ventilator may periodically or continuously calculate ventilatory data, e.g., a pressure drop ($\Delta P$) across the breathing tube from the patient wye to the carina, a pressure at the patient wye ($P_{wye}$), a resistance associated with the breathing tube (e.g., based on length, size, type of breathing tube), a gas density (e.g., based on $O_2$%), etc.

Ventilator 202 may further include a carinal pressure command module 224. According to some embodiments, carinal pressure command module 224 may calculate or determine a suitable carinal pressure command. According to embodiments, the work of breathing due to the breathing tube relative to the work required to maintain the carinal pressure command is targeted to be 0 joules/liter. For example, where the actual carinal pressure is equal to the carinal pressure command (i.e., $P_{carina} - P_{command} = 0$), the work of breathing relative to the work required to maintain the carinal pressure command is 0 joules/liter. In this case, the patient experiences this carinal pressure during exhalation and during inhalation just as if the breathing tube was not in place. As actual carinal pressure is difficult to measure, estimated carinal pressure is used as feedback control to target $P_{carina}$ at the $P_{command}$.

According to some embodiments, the carinal pressure command is PEEP. According to alternative embodiments, the carinal pressure command is calculated based on a pressure support ($P_{SUPP}$) setting. For example, if $P_{SUPP}$ is 10%, the carinal pressure command may be calculated as 10% of the PEEP setting. For example, if PEEP is 10 cm $H_2O$, the carinal pressure command may be determined to be 1 cm $H_2O$. In this case, while the $P_{carina}$ may equal $P_{command}$ (i.e., both equal to 10% of PEEP), the patient experiences less support for the tube resistance and the actual work of breathing is increased. According to embodiments, this may be done to challenge the patient (i.e., to promote weaning by increasing the patient's ability to breathe independently). According to other embodiments, the carinal pressure command is calculated as PEEP adjusted by an offset. For example, where PEEP is 0 cm $H_2O$, an offset may be used to subtract some value from 0 cm $H_2O$ to determine the carinal pressure command. According to still other embodiments, the carinal pressure command may be calculated based on a percentage of PEEP combined with an offset. According to embodiments, the carinal pressure command may be calculated via any suitable means.

Ventilator 202 may further include feedback control module 226. According to embodiments, feedback control module 226 may determine estimated $P_{carina}$ and calculate any error between the carinal pressure command and the estimated $P_{carina}$. Feedback control module 226 may determine estimated $P_{carina}$ via a any suitable means. For example, feedback control module 226 may determine estimated $P_{carina}$ by first measuring or estimating the pressure at the patient wye (measured or estimated $P_{wye}$) and adjusting for the dynamics of the breathing tube. $P_{wye}$ may be estimated or measured via any suitable means. For example, $P_{wye}$ may be measured using a sensor associated with the patient wye or may be estimated according to any other suitable means (e.g., by using pressure measurements at one or more other locations within the ventilatory system and calculating $P_{wye}$).

Upon measuring or estimating $P_{wye}$, the feedback control module 226 may determine estimated $P_{carina}$. According to embodiments, the dynamics of the breathing tube result in a pressure drop across the breathing tube ($\Delta P_{tube}$) between the patient wye and the patient's carina that is a function of one or more of a gas flow through the breathing tube, a breathing tube resistance (based on a size and type of the breathing tube), a gas composition (e.g., determined based on the $O_2$% or otherwise), an atmospheric pressure (e.g., measured or default of 0 cm$H_2O$), a humidity (e.g., measured or a default of 100% saturation), and a target inspiratory pressure (e.g., $P_I$ setting for mandatory ventilation or $P_{SUPP}$ setting for spontaneous ventilation). According to embodiments, $\Delta P_{tube}$ may be estimated or measured via any suitable means. Moreover, $\Delta P_{tube}$ may be continuously or periodically estimated or measured. Upon measuring or estimating $\Delta P_{tube}$, the feedback control module 226 may determine estimated $P_{carina}$ by subtracting the $\Delta P_{tube}$ from the $P_{wye}$ according to the following formula:

$$\text{Estimated } P_{carina} = P_{wye} - \Delta P_{tube}$$

Where $P_{wye}$ may be measured or estimated and $\Delta P_{tube}$ may be measured or estimated.

Upon determining estimated $P_{carina}$, the feedback control module 226 may determine an error between the carinal pressure command and the estimated $P_{carina}$. The feedback control module 226 may determine the error via any suitable means. For example, the feedback control module 226 may compare the carinal pressure command to the estimated $P_{carina}$ to determine the greater error. According to embodiments, if the carinal pressure command is greater than the estimated $P_{carina}$, the ventilator control algorithms may be modulated by some function of the error to increase the pressure at the carina. According other to embodiments, if the carinal pressure command is less than the estimated $P_{carina}$, ventilator control algorithms may be modulated by some function of the error to decrease the pressure at the carina. According to still other embodiments, if the carinal pressure command is substantially equal to the estimated $P_{carina}$, the feedback control module 226 may determine that a negligible or null error exists and the ventilator control algorithms may not be adjusted or modulated. According to embodiments, feedback control module 226 may modulate the ventilator control algorithms via any suitable means. According to embodiments, the feedback control module 226 may modulate the ventilator control algorithms substantially continuously (e.g., for every servo control period) or periodically (e.g., at the beginning of each inspiratory phase, every third inspiratory phase, or any other suitable periodic adjustment phase).

As should be appreciated, the various modules described above do not represent an exclusive array of modules. Indeed, any number of additional modules may be suitably configured to execute one or more of the above-described operations within the spirit of the present disclosure. Furthermore, the various modules described above do not represent a necessary array of modules. Indeed, any number of the disclosed modules may be appropriately replaced by other suitable modules without departing from the spirit of the present disclosure. According to some embodiments, operations executed by the various modules described above may be stored as computer-executable instructions in the ventilator memory, e.g., memory 112, which computer-executable instructions may be executed by one or more processors, e.g., processors 116, of the ventilator.

Figure 3:
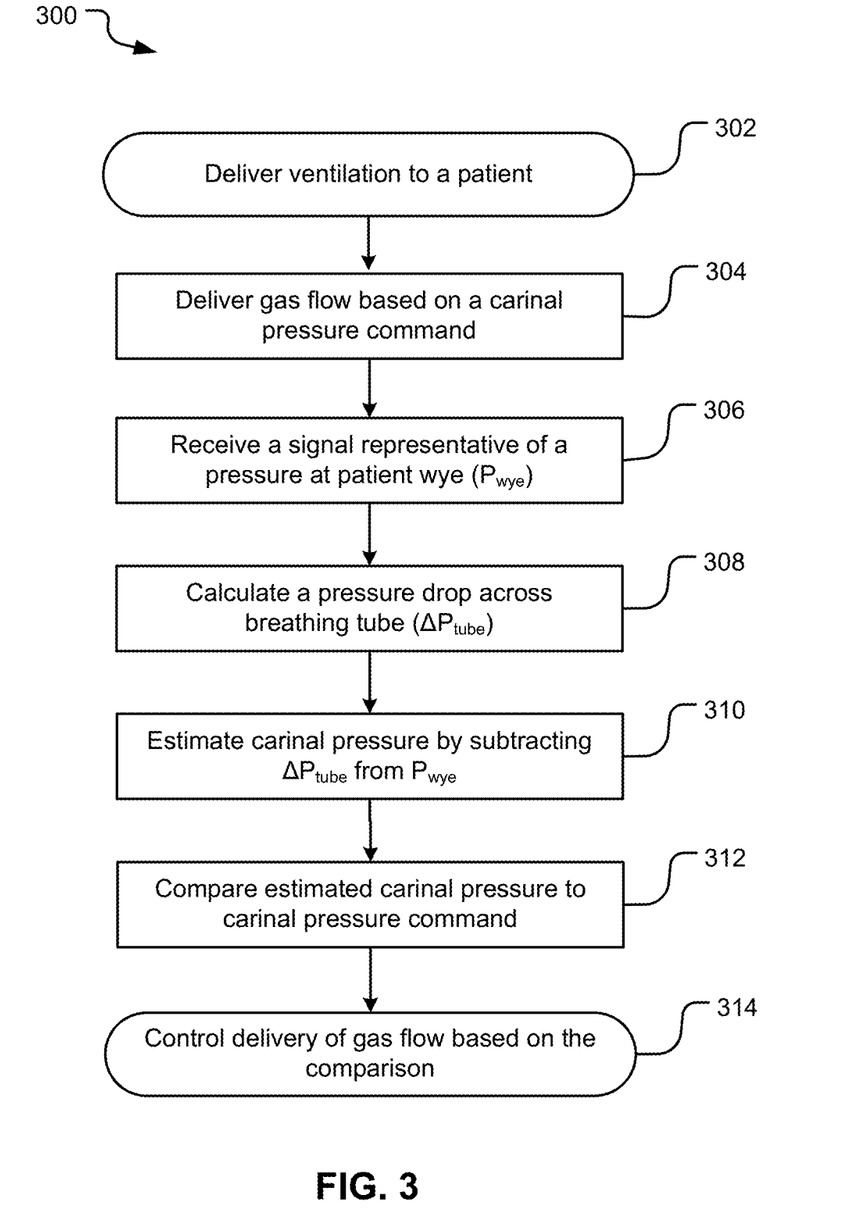
FIG. 3 is a flow chart illustrating an embodiment of a method for controlling delivery of gas flow to a patient.

FIG. 3 is a flow chart illustrating an embodiment of a method for controlling delivery of gas flow to a patient.

Method 300 begins with deliver ventilation operation 302. According to embodiments, ventilation involves delivering breathing gases to a patient who is unable to breathe completely independently. Ventilation includes delivering any portion of breathing gases, from full mandatory ventilation to full or partially-supported spontaneous ventilation.

At deliver operation 304, a gas flow may be delivered to a patient based on a carinal pressure command. The carinal pressure command may be a pressure that is maintained at the patient carina to minimize the work of breathing due to the breathing tube. According to embodiments, when the actual carinal pressure is equal to the carinal pressure command (i.e., $P_{carina} - P_{command} = 0$), the work of breathing relative to the work required to maintain the carinal pressure command is 0 joules/liter. In this case, the patient experiences this pressure during exhalation and during inhalation just as if the breathing tube was not in place. As actual carinal pressure is difficult to measure, estimated carinal pressure is used as feedback control to target $P_{carina}$ at the $P_{command}$.

According to some embodiments, the carinal pressure command is equal to PEEP. According to alternative embodiments, the carinal pressure command is some function of PEEP. For example, according to embodiments, the carinal pressure command is calculated based on a pressure support ($P_{SUPP}$) setting. For example, if $P_{SUPP}$ is 10%, the carinal pressure command may be calculated as 10% of the PEEP setting. According to other embodiments, PEEP may be adjusted by an offset to determine the carinal pressure command. For example, where PEEP is 0 cm $H_2O$, an offset may be used to subtract some value from 0 cm $H_2O$ to calculate the carinal pressure command. According to still other embodiments, the carinal pressure command may be calculated based on a percentage of PEEP combined with an offset. According to other embodiments, the carinal pressure command is calculated or determined via any suitable means.

At receive operation 306, a signal representative of a pressure at the patient wye ($P_{wye}$) may be received. As described above, the patient wye couples a breathing tube (e.g., patient interface 180) to an inspiratory limb and an expiratory limb of the ventilation tubing system. The pressure at the patient wye may be measured using a sensor associated with the patient wye or may be estimated according to any suitable means (e.g., by using pressure measurements at one or more other locations within the ventilatory system and calculating $P_{wye}$). As such, the signal representative of $P_{wye}$ may be an estimated $P_{wye}$ or a measured $P_{wye}$.

At calculate operation 308, a pressure drop across the breathing tube ($\Delta P_{tube}$) may be calculated. In general, the dynamics of the breathing tube result in a pressure drop across the breathing tube ($\Delta P_{tube}$) between the patient wye and the patient's carina that is a function of one or more of a gas flow through the breathing tube, a breathing tube resistance (based on a size and type of the breathing tube), a gas composition (e.g., determined based on the $O_2$% or otherwise), an atmospheric pressure (e.g., measured or default of 0 cm$H_2O$), a humidity (e.g., measured or a default of 100% saturation), and a target inspiratory pressure (e.g., $P_I$ setting for mandatory ventilation or $P_{SUPP}$ setting for spontaneous ventilation). According to embodiments, $\Delta P_{tube}$ may be estimated or measured via any suitable means. Moreover, $\Delta P_{tube}$ may be continuously or periodically estimated or measured.

At estimate operation 310, a carinal pressure may be estimated. In general, patient's carina is a cartilaginous ridge located at the site of the tracheal bifurcation between the two primary bronchi. Due to the location of the carina, it is difficult to measure an actual carinal pressure. An estimated carinal pressure (estimated $P_{carina}$) refers to a pressure estimated to exist at the patient carina. According to embodiments, the carinal pressure may be estimated by subtracting $\Delta P_{tube}$ from $P_{wye}$ according to the following formula:

$$\text{Estimated } P_{carina} = P_{wye} - \Delta P_{tube}$$

Where $\Delta P_{tube}$ may be measured or estimated and $P_{wye}$ may be measured or estimated.

At compare operation 312, the estimated $P_{carina}$ may be compared to carinal pressure command. As described above, when the estimated $P_{carina}$ is equal to the carinal pressure command, the work of breathing due to the breathing tube relative to the work required to maintain the carinal pressure command is targeted at 0 joules/liter. According to some embodiments, the carinal pressure command is equal to PEEP, to some percentage of PEEP, or to PEEP adjusted by an offset. According to embodiments, the estimated $P_{carina}$ may be compared to carinal pressure command via any suitable means.

At control delivery operation 314, the delivery of gas flow to the patient may be controlled based on comparing the estimated $P_{carina}$ to the carinal pressure command. Based on the comparison, the ventilator control algorithms may be modulated accordingly. For example, if the carinal pressure command is greater than the estimated $P_{carina}$, ventilator control algorithms may be modulated by some function of the error to increase the pressure at the carina. According other to embodiments, if the carinal pressure command is less than the estimated $P_{carina}$, the ventilator control algorithms may be modulated by some function of the error to decrease the pressure at the carina. According to still other embodiments, if the carinal pressure command is substantially equal to the estimated $P_{carina}$, the ventilator control algorithms may not be adjusted or modulated.

As should be appreciated, the particular steps and methods described above with reference to FIG. 3 are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

Figure 4:
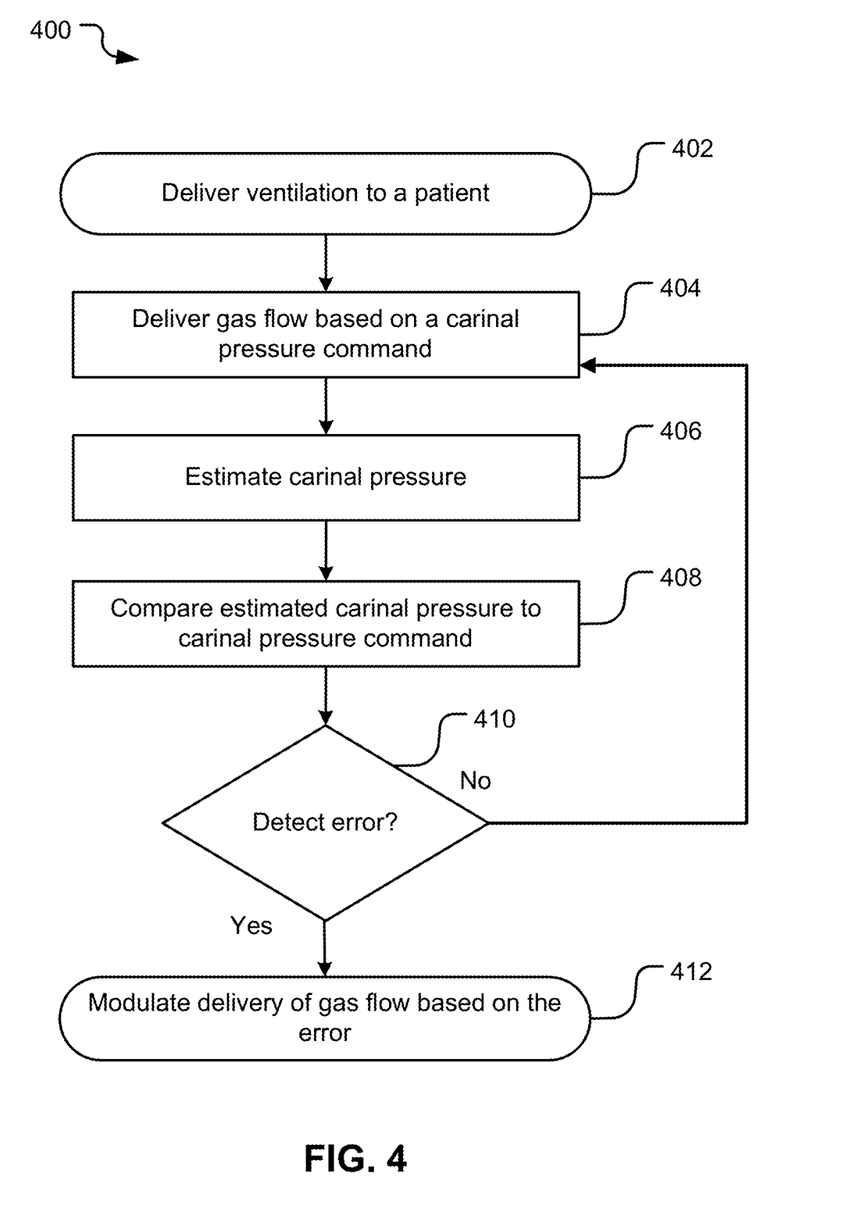
FIG. 4 is a flow chart illustrating an embodiment of a method for modulating ventilator control algorithms based on an estimated carinal pressure.

FIG. 4 is a flow chart illustrating an embodiment of a method for modulating ventilator control algorithms based on an estimated carinal pressure.

Method 400 begins with deliver ventilation operation 402. As described above, ventilation involves delivering breathing gases to a patient who is unable to breathe completely independently. Ventilation includes delivering any portion of breathing gases, from full mandatory ventilation to full or partially-supported spontaneous ventilation.

At deliver operation 404, a gas flow may be delivered to a patient based on a carinal pressure command, as described above with respect to deliver operation 304.

At estimate operation 406, a carnal pressure may be estimated. As described above with respect to estimate operation 310, the carinal pressure may be estimated by subtracting $\Delta P_{tube}$ from $P_{wye}$ according to the following formula:

$$\text{Estimated } P_{carina} = P_{wye} - \Delta P_{tube}$$

Where $\Delta P_{tube}$ may be measured or estimated and $P_{wye}$ may be measured or estimated.

At compare operation 408, the estimated $P_{carina}$ may be compared to the carinal pressure command. According to some embodiments, by comparing the estimated $P_{carina}$ the carinal pressure command an error may be determined. The error may be determined via any suitable means. For example, the estimated $P_{carina}$ may be subtracted from the carinal pressure command to determine a difference between the estimated $P_{carina}$ and the carinal pressure command. According to some embodiments, if the estimated $P_{carina}$ is greater than the carinal pressure command, the error may be negative. According to alternative embodiments, if the estimated $P_{carina}$ is less than the carinal pressure command, the error may be positive. According to still alternative embodiments, if the estimated $P_{carina}$ is substantially equal to the carinal pressure command, there may be no error.

At determination operation 410, it may be determined whether an error was detected upon comparing the estimated $P_{carina}$ to the carinal pressure command. As described above, upon comparing the estimated $P_{carina}$ to the carinal pressure command, a negative error, a positive error, or no error may be detected. If a negative error or a positive error is detected, the method may proceed to modulate operation 412. Alternatively, if no error is detected, the method may return to deliver operation 404. According to additional or alternative embodiments, the error (whether positive or negative) may be compared to an error threshold. According to some embodiments, if the error is less than the error threshold, the error may be negligible and the method may return to deliver operation 404. According to other embodiments, if the error is greater than or equal to the error threshold, the error may not be negligible and the method may proceed to modulate operation 412.

At modulate delivery operation 412, the delivery of gas flow may be modulated based on the error. For example, if the estimated $P_{carina}$ is greater than the carinal pressure command (e.g., negative error) ventilator control algorithms may be modulated by some function of the error to adjust gas flow to decrease the pressure at the carina. According to alternative embodiments, if the estimated $P_{carina}$ is less than the carinal pressure command (e.g., positive error) ventilator control algorithms may be modulated by some function of the error to adjust gas flow to increase the pressure at the carina. As should be appreciated, if the estimated $P_{carina}$ is substantially equal to the carinal pressure command (e.g., no error), ventilator control algorithms may not be adjusted or modulated.

According to embodiments, the ventilator control algorithms may be modulated via any suitable means. That is, according to embodiments, the modulated ventilator control algorithms are adjusted to maintain the carinal pressure command such that the work of breathing due to the breathing tube relative to the work required to maintain the carinal pressure command approximates 0 joules/liter. According to embodiments, the ventilator control algorithms may be modulated substantially continuously (e.g., for every servo control period) or periodically (e.g., at the beginning of each inspiratory phase, every third inspiratory phase, or any other suitable periodic adjustment phase).

As should be appreciated, the particular steps and methods described above with reference to FIG. 4 are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

Figure 5:
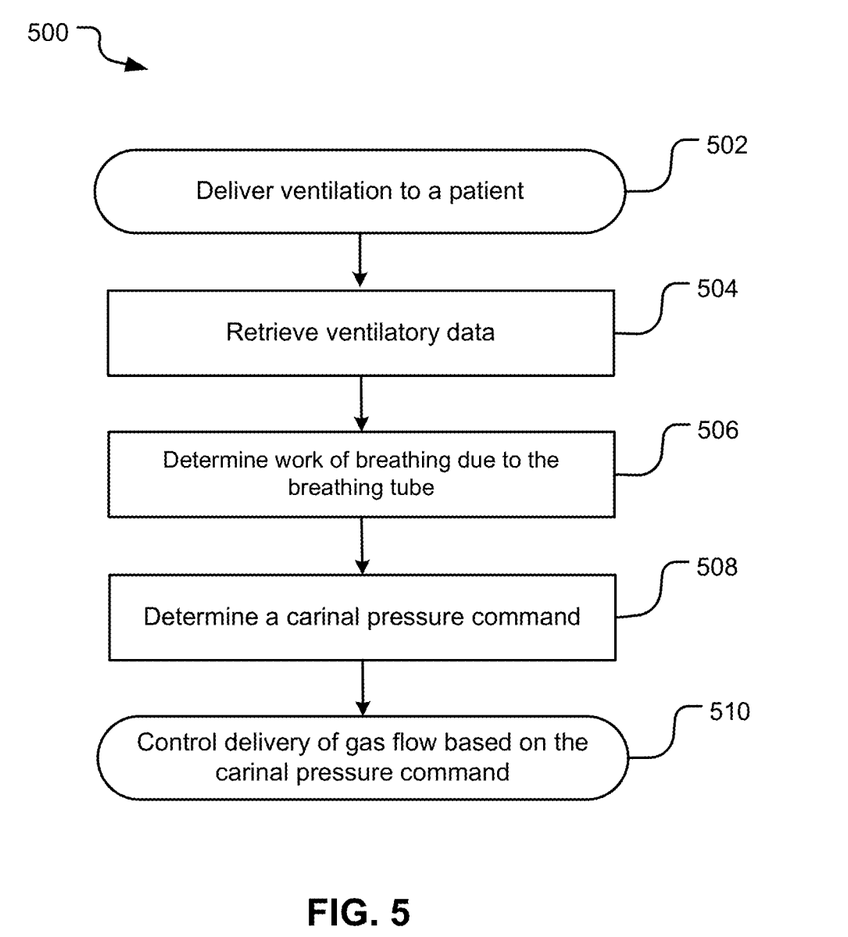
FIG. 5 is a flow chart illustrating an embodiment of a method for determining a carinal pressure command based on a pressure support setting.

FIG. 5 is a flow chart illustrating an embodiment of a method for determining a carnal pressure command based on a pressure support setting.

Method 500 begins with deliver ventilation operation 502. According to embodiments, ventilation involves delivering breathing gases to a patient who is unable to breathe completely independently. Ventilation includes delivering any portion of breathing gases, from full mandatory ventilation to full or partially-supported spontaneous ventilation.

At retrieve operation 504, ventilatory data may be retrieved via any suitable means. As described above, ventilatory data may comprise any data regarding ventilatory settings (e.g., $O_2$%, PEEP, $P_I$, $P_{SUPP}$, etc.), patient data (e.g., ideal body weight, IBW), breathing tube data (e.g., diameter, length, type, and/or resistance of breathing tube), atmospheric pressure data (e.g., measured or default of 0 $cmH_2O$), humidity data (e.g., measured or default of 100% saturation), etc. Retrieved ventilatory data may be acquired from any suitable database or data storage location associated with the ventilator (e.g., stored in memory on the ventilator, stored on a server accessible over a network, etc.). According to additional embodiments, ventilatory data may be retrieved that has been periodically or continuously calculated by the ventilator. For example, retrieved ventilatory data may further include a pressure drop ($\Delta P$) across the breathing tube (e.g., from the patient wye to the carina), a pressure at the patient wye ($P_{wye}$), a resistance associated with the breathing tube (e.g., based on length, size, type of breathing tube), a gas density (e.g., based on $O_2$%), etc. Indeed, any suitable measured, calculated, and/or graphically represented ventilatory data may be retrieved at retrieve operation 504.

At determine operation 506, the work of breathing due to the breathing tube may be determined. Any suitable ventilatory data retrieved above, whether with regard to the breathing tube, the patient, the atmosphere or humidity, the ventilatory settings, gas flow, etc., may be used to determine the work of breathing associated with the tube. For example, the work of breathing associated with the tube may be influenced by the resistance of the breathing tube (resulting from the diameter, length, and type of tube), the gas flow, the gas composition, etc.

At determine operation 508, a carinal pressure command may be determined. According to embodiments, the carinal pressure command is targeted to offset the work of breathing due to the breathing tube relative to the work required to maintain the carinal pressure command. That is, the work of breathing due to the breathing tube relative to the work required to maintain the carinal pressure command is targeted at 0 joules/liter. For example, where the actual carinal pressure is equal to the carinal pressure command (i.e., $P_{carina} - P_{command} = 0$), the work of breathing relative to the work required to maintain the carinal pressure is 0 joules/liter.

The carinal pressure command may be determined or calculated according to any suitable means. For example, according to embodiments, the carinal pressure command may be PEEP. According to alternative embodiments, the carinal pressure command may be some function of PEEP. For example, where $P_{SUPP}$ is 10%, the carinal pressure command may be calculated as 10% of PEEP. According to still other embodiments, PEEP may be adjusted by an offset to determine the carinal pressure command. Indeed, the carinal pressure command may be calculated or determined via any suitable means.

At control delivery operation 510, a gas flow may be delivered to a patient based on the carinal pressure command. According to embodiments, one or more ventilator control algorithms may be employed to deliver gas flow to the patient based on the carinal pressure command. Moreover, an estimated carinal pressure may be determined and used as feedback control of the ventilator control algorithms in order to achieve the carinal pressure command at the carina. According to additional embodiments, when the carinal pressure command is maintained at the carina, the work of breathing due to the breathing tube relative to the work required to maintain the carinal pressure command is 0 joules/liter.

As should be appreciated, the particular steps and methods described above with reference to FIG. 5 are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

Unless otherwise indicated, all numbers expressing measurements, dimensions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5, etc. This same principle applies to ranges reciting only one numerical value. Furthermore, such an interpretation should apply regardless of the breadth of the range or the characteristics being described.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A ventilator-implemented method for controlling delivery of gas flow to a patient, the method comprising:

delivering gas flow to the patient based on a carinal pressure command;

receiving a signal representative of a pressure at a patient wye;

calculating a pressure drop across a breathing tube extending from the patient wye to about the carina of the patient;

estimating a carinal pressure by subtracting the pressure drop across the breathing tube from the pressure at the patient wye;

comparing the estimated carinal pressure to the carinal pressure command; and controlling delivery of gas flow to the patient based on comparing the estimated carinal pressure and the carinal pressure command.

2. The method of claim 1, wherein the pressure drop is estimated as a function of at least one of: a gas flow through the breathing tube, atmospheric pressure, humidity, a gas composition, and a target inspiratory pressure.

3. The method of claim 1, wherein controlling delivery of gas flow to the patient further comprises:

determining an error based on comparing the estimated carinal pressure and the carinal pressure command; and modulating the delivery of gas flow based on the error.

4. The method of claim 3, wherein the delivery of gas flow is adjusted based on the error when the estimated carinal pressure is less than the carinal pressure command.

5. The method of claim 3, wherein the delivery of gas flow is adjusted based on the error when the estimated carinal pressure is greater than the carinal pressure command.

6. The method of claim 1, wherein the signal representative of the pressure at the patient wye represents an estimated pressure at the patient wye.

7. The method of claim 1, wherein the carinal pressure command is one of: positive end expiratory pressure (PEEP), a percentage of PEEP, and PEEP adjusted by an offset.

8. A ventilator system for controlling delivery of gas flow to a patient, the ventilator system comprising:
- at least one processor; and
- at least one memory communicatively coupled to the at least one processor and containing instructions that, when executed by the at least one processor, cause the ventilator system to:
  - deliver gas flow to the patient based on a carinal pressure command;
  - receive a signal representative of a pressure at a patient wye;
  - calculate a pressure drop across a breathing tube extending from the patient wye to about the carina of the patient;
  - estimate a carinal pressure by subtracting the pressure drop across the breathing tube from the pressure at the patient wye;
  - compare the estimated carinal pressure to the carinal pressure command; and
  - control delivery of gas flow to the patient based on comparing the estimated carinal pressure and the carinal pressure command.

9. The ventilator system of claim 8, wherein the pressure drop is estimated as a function of at least one of: a gas flow through the breathing tube, atmospheric pressure, humidity, a gas composition, and a target inspiratory pressure.

10. The ventilator system of claim 8, wherein controlling delivery of gas flow to the patient further comprises:
- determining an error based on comparing the estimated carinal pressure and the carinal pressure command; and
- modulating the delivery of gas flow based on the error.

11. The ventilator system of claim 10, wherein the delivery of gas flow is adjusted based on the error when the estimated carinal pressure is less than the carinal pressure command.

12. The ventilator system of claim 10, wherein the delivery of gas flow is adjusted based on the error when the estimated carinal pressure is greater than the carinal pressure command.

13. The ventilator system of claim 8, wherein the signal representative of the pressure at the patient wye represents an estimated pressure at the patient wye.

14. The ventilator system of claim 8, wherein the carinal pressure command is one of: positive end expiratory pressure (PEEP), a percentage of PEEP, and PEEP adjusted by an offset.

15. A ventilator processing interface for controlling delivery of gas flow to a patient, the ventilator processing interface comprising:
- means for delivering gas flow to the patient based on a carinal pressure command;
- means for receiving a signal representative of a pressure at a patient wye;
- means for calculating a pressure drop across a breathing tube extending from the patient wye to about the carina of the patient;
- means for estimating a carinal pressure by subtracting the pressure drop across the breathing tube from the pressure at the patient wye;
- means for comparing the estimated carinal pressure to the carinal pressure command; and
- means for controlling delivery of gas flow to the patient based on comparing the estimated carinal pressure and the carinal pressure command.

16. The ventilator processing interface of claim 15, wherein the controlling means for delivery of gas flow to the patient further comprises:
- means for determining an error based on the comparison of the estimated carinal pressure and the carinal pressure command; and
- means for modulating the delivery of gas flow based on the error.

17. The ventilator processing interface of claim 15, wherein the signal representative of the pressure at the patient wye represents an estimated pressure at the patient wye.

18. The ventilator processing interface of claim 15, wherein the carinal pressure command is one of positive end expiratory pressure (PEEP), a percentage of PEEP, and PEEP adjusted by an offset.

19. A non-transitory computer storage medium having computer-executable instructions that when executed by a processor cause a ventilator system to:
- deliver gas flow to the patient based on a carinal pressure command;
- receive a signal representative of a pressure at a patient wye;
- calculate a pressure drop across a breathing tube extending from the patient wye to about the carina of the patient;
- estimate a carinal pressure by subtracting the pressure drop across the breathing tube from the pressure at the patient wye;
- compare the estimated carinal pressure to the carinal pressure command; and
- control delivery of gas flow to the patient based on comparing the estimated carinal pressure and the carinal pressure command.

20. The non-transitory computer storage medium of claim 19, wherein controlling delivery of gas flow to the patient further comprises:
- determining an error based on comparing the estimated carinal pressure and the carinal pressure command; and
- modulating the delivery of gas flow based on the error.

* * * * *